(12) United States Patent
Yeoman et al.

(10) Patent No.: US 8,821,933 B2
(45) Date of Patent: Sep. 2, 2014

(54) POLYMERS AND HYDROGELS

(75) Inventors: Roy R. Yeoman, Burke, VA (US); Adrian S. Fox, Surprize, AZ (US)

(73) Assignee: nanoDERM Sciences, Inc., Derwood, MD (US)

( * ) Notice: Subject to any disclaimer, the term of this patent is extended or adjusted under 35 U.S.C. 154(b) by 115 days.

(21) Appl. No.: 13/286,320

(22) Filed: Nov. 1, 2011

(65) Prior Publication Data

US 2012/0107369 A1 May 3, 2012

Related U.S. Application Data

(60) Provisional application No. 61/538,895, filed on Sep. 25, 2011, provisional application No. 61/344,872, filed on Nov. 1, 2010.

(51) Int. Cl.

| | | |
|---|---|---|
| *A61K 9/00* | (2006.01) |
| *A61P 17/02* | (2006.01) |
| *C08G 65/331* | (2006.01) |
| *B82Y 5/00* | (2011.01) |
| *A61L 26/00* | (2006.01) |
| *C08J 3/075* | (2006.01) |
| *A61L 15/28* | (2006.01) |
| *A61L 15/44* | (2006.01) |
| *A61L 27/54* | (2006.01) |
| *A61K 9/06* | (2006.01) |
| *C08B 37/02* | (2006.01) |
| *A61L 27/52* | (2006.01) |
| *C08L 63/00* | (2006.01) |
| *A61L 27/20* | (2006.01) |
| *C08L 5/02* | (2006.01) |
| *A61K 47/36* | (2006.01) |

(52) U.S. Cl.
CPC ............ *B82Y 5/00* (2013.01); *A61L 26/008* (2013.01); *A61L 26/0023* (2013.01); *C08J 3/075* (2013.01); *A61L 15/28* (2013.01); *C08J 2305/02* (2013.01); *A61L 15/44* (2013.01); *A61L 27/54* (2013.01); *A61K 9/06* (2013.01); *C08B 37/0021* (2013.01); *A61L 27/52* (2013.01); *C08L 63/00* (2013.01); *A61L 27/20* (2013.01); *C08L 5/02* (2013.01); *A61L 26/0066* (2013.01); *A61K 47/36* (2013.01)
USPC ............ 424/487; 424/400; 424/485; 424/488

(58) Field of Classification Search
USPC .................................................. 424/400, 484
See application file for complete search history.

(56) References Cited

U.S. PATENT DOCUMENTS 6,696,089 B2 * 2/2004 Kabanov et al. ............. 424/484

* cited by examiner

*Primary Examiner* — Walter Webb
(74) *Attorney, Agent, or Firm* — Bernard G. Pike; Pike IP Law, PLLC

(57) ABSTRACT

Methods and compositions related polymers and hydrogels. In some cases to biodegradable hydrogels for use in medical applications are disclosed. The polymers and hydrogels may be produced from cross-linked dextran and poly(epoxides). The poly(epoxides) may be poloxamers.

9 Claims, 2 Drawing Sheets

POLYMERS AND HYDROGELS

RELATED APPLICATIONS

This application claims priority under 35 U.S.C. §119 to U.S. Provisional Patent Application No. 61/538,895 filed on Sep. 25, 2011 and U.S. Provisional Patent Application No. 61/344,872 filed on Nov. 1, 2010.

TECHNICAL FIELD

The invention is related to hydrogels. The hydrogels are cross-linked copolymers that may be used for various applications including, but not limited to, drug delivery. Embodiments of the hydrogels may comprise a plurality of polymer segments derived from a polysaccharide such as, but not limited to, dextran, and a plurality of polymer segments derived from epoxide monomers such as, but not limited to, a poloxamer.

BACKGROUND

Hydrogels comprise a network of polymer chains that are hydrophilic. The hydrogels may swell by the addition of a liquid. Hydrogels are cross-linked highly absorbent natural or synthetic polymers. Hydrogels may also possess a degree of flexibility very similar to natural tissue, due to their significant liquid holding capability. Common uses for hydrogels include drug delivery systems, contact lenses, medical implants, scaffolds in tissue engineering, sustained-release drug delivery systems, as absorbents in disposable diapers, EEG and ECG medical electrodes, water gel explosives, dressings for healing of burn or other hard-to-heal wounds, and reservoirs in topical drug delivery particularly topical drug delivery of ionic drugs delivered by iontophoresis, for example. Common polymeric precursors include, for example, polyvinyl alcohol, sodium polyacrylate, acrylate polymers and copolymers with a plurality of hydrophilic groups.

There exists a need for biocompatible, biodegradable hydrogels for medical applications such as wound healing and drug delivery.

DESCRIPTION OF EMBODIMENTS

Figure 1:
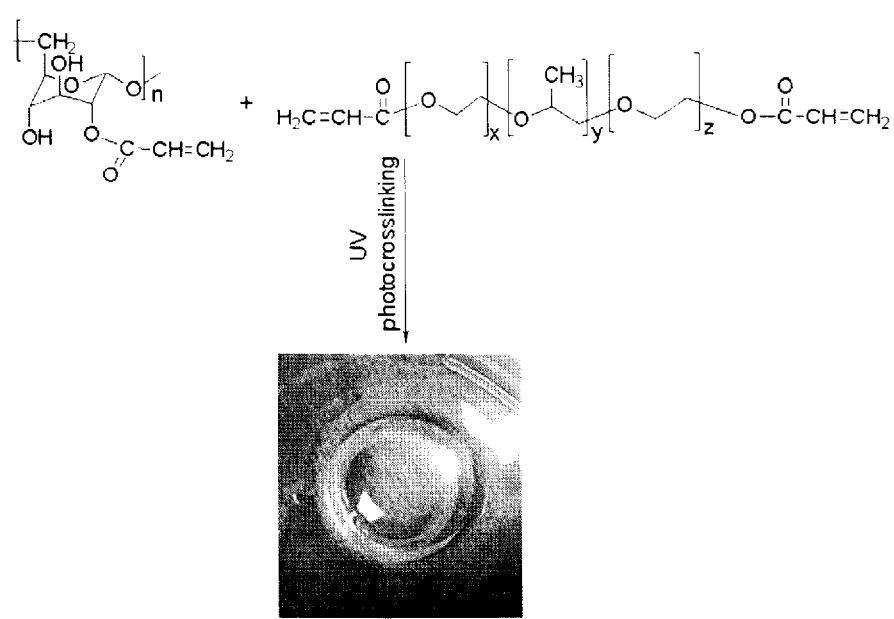
FIG. 1 is a chemical equation showing the cross-linking of a functionalized dextran with functionalized poloxamer, Pluronic™ 127, to form the hydrogel shown in the photograph.

In one aspect, the invention is directed to a polymeric network. The polymeric network may be cross-linked with chemically or ionizing radiation such as gamma or beta radiation. Other embodiments may result in cross-linking with ionic bonds with polyvalent metals, organic materials having an ionic charge. The cross-linking may be chemically cross-linking. In one embodiment, the cross-linked polymeric network comprises a plurality of first polymeric segments derived from epoxide monomers (also referred to as "poly (epoxide)") and a plurality of second polymeric segments derived from a polysaccharide. The polysaccharide may comprise biodegradable glycosidic bonds. The first polymeric segments and the second polymeric segments may be bonded together to form a polymeric network. Such a polymeric network may be used as a drug delivery patch, a sustained release drug delivery system, a wound healing gel, a dressing for healing a burn, a smart gel capable of delivering drugs due to changes in their environment such as a temperature change or pH change, as well as other applications.

The polymeric network may be chemically cross-linked, wherein linking groups connect the first polymeric segments to the second polymeric segments to form a polymeric network. For example, dextran can be functionalized with a first cross-linkable functional group and the polymer derived from epoxide monomers, such as a poloxamer, can be functionalized with a complementary cross-linkable functional group. A complementary cross-linkable functional group may be any group that can react or otherwise form a bond or linking group between the polymeric segments. The two functional groups attached to the polymeric monomers may react to form the polymeric network or react with a cross-linking agent to form the polymeric network.

In a specific embodiment, both the polysaccharide and poly(epoxide) may be functionalized with cross-linkable double bonds. The cross-linking groups may comprise an ester group. After cross-linking in some embodiments, the linking groups may comprise at least two ester groups. In certain embodiments for biomedical applications, the hydrogel, cross-linked network, and/or the block copolymer comprising a polysaccharide and a poloxamer includes a biocompatible linking group. The biocompatible linking group would not include functional groups that show significant toxicity to the patient either in the polymeric form or the residues of biodegradation. A compound would show significant toxicity if the compound was denied approval by the FDA for use in a certain therapeutic application.

In certain embodiments of the polymeric network, the block copolymer of epoxides is a triblock copolymer. The block copolymer may comprise at least one block derived from propylene oxide monomers and at least one block derived from ethylene oxide monomers. In a further embodiment, the block copolymer of epoxides is an ABA triblock copolymer wherein the A block is derived from ethylene oxide monomers and the B block is derived from propylene oxide monomers, such as a poloxamer.

In one embodiment, the drug delivery system may be a thermo-responsive biodegradable polymeric hydrogel. In a more specific embodiment, the hydrogel comprises dextran polymeric segments and poloxamer polymeric segments that are cross-linked. The hydrogel may be thermally responsive due to the interaction of the poloxamer segments with water. Poloxamers may form reversible gels. A reversible gels refer to gels comprising components that have the capacity to make, break, and modify the bonds responsible for holding the network together. Gels that do not have this capability because they are held together by covalent bonds are termed permanent gels. Pluronic F-127 (Poloxamer 407, PF-127) forms a thermoreversible gel. This characteristic has allowed PF-127 to be used as a carrier for most routes of administration including oral, topical, intranasal, vaginal, rectal, ocular, and parenteral routes. At low temperatures in aqueous solutions, a hydration layer surrounds PF-127 molecules. However, when the temperature is raised, the hydrophilic chains of the copolymer become dehydrated as a result of the breakage of the hydrogen bonds that had been established between the solvent and these chains. Reverse thermal gelation and low toxicity have been the basis of research into the use of PF-127 as a possible drug delivery system in man. It has been considered for topical delivery of lidocaine, anti-cancer agents, and for the covering of burnt wounds. This feature of poloxamers may be exploited in covalently bonded hydrogels. As the structure of the poloxamer portion of the hydrogel changes in response to temperature, the structure and the capacity of the hydrogel to hold liquid components changes allowing targeted wound healing or drug delivery applications.

Among the natural polymers, dextran is a colloidal, hydrophilic, and nontoxic polysaccharide. Dextran can be biodegraded by dextranase, which exists in mammalian (including human) tissues. Among the natural polymers, dextran is a colloidal, hydrophilic, and nontoxic polysaccharide composed of linear α-1,6-linked D-glucopyranose residues with a low fraction of -1,2, -1,3 and -1,4 linked side chains. From a structural point of view, dextran has reactive hydroxyl groups that can be modified to form reactive end groups which may be used for cross-linking or otherwise functionalizing the hydrogel. For example, the saccharide may be functionalized allyl isocyanate (AI), ethylamine (AE), chloroacetic acid (AC) and/or maleic anhydride (AM), for example.

The dextran precursor and polymeric segments are both enzymatically and hydrolytically degradable. In addition, the poloxamer may be water soluble and temperature sensitive to normal body temperatures. For example, when the hydrogel is applied to or taken within the body, the hydrogel will release at least a portion of a retained medicament. Additionally, these dextran hydroxyl groups provide a vehicle for tunable hydrogels. Adjusting the chemical cross-linking protocol such as the degree of cross-linking and/or the chain length of the polymeric segments can produce predetermined variations of the hydrogel structure, porosity, chemical bonds, thermoresponsiveness and mechanical strength.

The hydrogel can act as a "smart, super sponge" and/or has the capability of dispensing a wound healing solution facilitated by body temperature over a period of time and will result in a controlled and continuous wound therapy for patients.

As used herein, "polysaccharide" means a polymeric carbohydrate having a chemical structure formed of repeating units including mono-saccharides or di-saccharides joined together by glycosidic bonds. The polysaccharide may be linear or branched, homopolysaccharide or heteropolysaccharides (Polysaccharides comprising modifications of the repeating unit). The polysaccharides may be amorphous or crystalline. The term "polysaccharide" includes polysaccharides that have been modified by a reaction of its hydroxyl groups or other group with a compound to a different pendent functional group. Particular embodiments of the saccharides are storage polysaccharides and biodegradable saccharides. As used herein, "biodegradable saccharides" are saccharides that may be biodegradable by enzymes present in an animal. Additionally, the saccharide hydroxyl groups provide a vehicle for producing "tunable" hydrogels. Adjusting the chemical cross-linking protocol of dextran to the block copolymer poloxamer can produce predetermined variations of the chemical bonds and the properties of the dextran hydrogel for example, mechanical strength, swelling, diffusion, degradation etc. The dextran-poloxamer hydrogel synthesis can be optimized per the specific application for controlled drug delivery and duration of prescribed therapy. See Examples. Preferably, in specific embodiments, the polysaccharides are linear or branched (noncyclic) polysaccharides.

In certain embodiments, the polysaccharide may be a glucan. As used herein, a glucan is a polysaccharide comprising a plurality of glucose molecules linked together by glycosidic bonds. Examples of glucans are, but not limited to, dextran, laminarin, and lichenin. For example, dextran is a complex, branched glucan comprising polymeric branches varying in length from 3 to 2000 kilodaltons. In dextran, a straight chain comprising α-1,6 glycosidic linkages between glucose molecules with branches connected from α-1,3 linkages. Dextran is a bacterial polysaccharide and may be synthesized from sucrose by certain lactic-acid bacteria, for example, *Leuconostoc mesenteroides* and *Streptococcus mutans*. In certain embodiments, the polymeric network may comprise dextran bonded to a block copolymer of epoxides such as a poloxamer. Dextran has long been employed as an IV blood substitute demonstrating biocompatibility. Dextranase, found throughout the body, can enzymatically degrade dextran making it an candidate for a hydrogel with in vivo applications.

As used herein, the polymers of epoxides (or poly(epoxides)) may be homopolymers, copolymers including random, block copolymers, and/or copolymers comprising at least two blocks different epoxides such as, for example, a poloxamer. An epoxide is a cyclic ether with only three ring atoms. The simplest epoxide is ethylene oxide, also known as oxirane. Additional epoxides include, but are not limited to, ethylene oxide, propylene oxide, butylene oxide and derivatives of these compounds. In one embodiment, the block copolymer of epoxides may be a block of hydrophobic polyoxypropylene (poly(propylene oxide)) and a block of hydrophilic polyoxyethylene (poly(ethylene oxide)). In some embodiments, the block copolymer of epoxides may include additional blocks as desired to produce the desired physical properties. In some embodiments, the block copolymer of epoxides may preferably be a poloxamer. Many different poloxamers exist that have slightly different properties. For the generic term "poloxamer", these copolymers are commonly named with the letter "P" (for poloxamer) followed by three digits, the first two digits×100 give the approximate molecular mass of the polyoxypropylene core, and the last digit×10 gives the percentage polyoxyethylene content (for example, P407=Poloxamer with a polyoxypropylene molecular mass of 4,000 g/mol and a 70% polyoxyethylene content). In certain embodiments, the poloxamer may comprise a polyoxypropylene molecular mass in the range of 2,000 to 6,000 g/mol; in further embodiments, the polyoxypropylene molecular mass may be in the range of 2,500 to 5,000 g/mol. Additionally, the poloxoamer may have from 30% to 90% polyoxyethylene content; in further embodiments, the poloxamer may have a polyoxyethylene in the range of 60% to 80%.

As used herein, poloxamers are nonionic triblock copolymers composed of a central hydrophobic chain of polyoxypropylene (poly(propylene oxide)) connected to two hydrophilic chains of polyoxyethylene (poly(ethylene oxide)). Poloxamers are triblock ABA copolymers wherein the A blocks are hydrophilic and the B block is hydrophobic. Poloxamers are available through BASF™ under the trade name PLURONIC™. Poloxmers were described in U.S. Pat. No. 3,740,421, which is hereby incorporated by reference.

The lengths of the polymer blocks of poloxamer may be customized individually. The general formula for a poloxamer is shown in Formula 1:

$$HO(CH_2CH_2O)_x(CH_2CH(CH_3)O)_y(CH_2CH_2O)_zH \quad \text{(Formula 1)}$$

The saccharide block may be hydrophilic and the block comprising epoxide monomers comprise both hydrophobic and hydrophilic segments. The copolymer reaction mixture, prior to cross-linking, may be a blend of a water soluble, very hydrophilic polysaccharide monomer, and/or a water soluble, hydrophilic (poly(ethylene oxide) and hydrophobic (poly (propylene oxide)) ABA block terpolymer. As such, a copolymer mixture comprising such polymers may self-organize into hydrophilic regions and hydrophobic regions. A crosslinking process may then be used to fix this structure, resulting in a polymeric network or hydrogel with specific regions with different properties. These phase separated, or hard and soft regions (or hydrophobic and hydrophilic areas) within the hydrogel structure tend to self-arrange and form three dimensional areas in gel that attract similarly charged species in the solution. The specific regions may be visible to the naked eye upon cool down of the hydrogel.

In one embodiment, the hydrogel is a unique, biocompatible, and biodegradable, cross-linked hydrogel platform for use as a wound dressing capable of maintaining a moist wound environment that would encourage the wound healing process. The hydrogel may be a biocompatible, as well as biodegradable by endogenous glycosides and esterases, three dimensionally crosslinked hydrogel platform. Using, for example, electron beam crosslinking of a blend of diacryloyl or dimethacryloyl terminated polysaccharide (Dextran) and a diacryloyl or dimethacryloyl terminated triblock copolymer, poly-(ethylene oxide)-b-(propylene oxide)-b-(ethylene oxide), a broad spectrum of hydrogel platforms and porosities can be fashioned for moist wound dressings, and wound healing enhancers. These platforms with controlled porosity can deliver drugs and other medicaments topically, transdermally, orally, and for deep cavity wound applications.

Embodiments of the hydrogel may be considered to be a smart super sponge that is tunable by adjusting the chemical cross-linking protocol that produces variations of the chemical bonds and their mechanical strength. The capability of dispensing a deliverable can be facilitated by body temperature over a period of time and will result in a controlled and continuous delivery system for dispensing drugs and other medicaments topically, transdermally, orally, wound treatment and application to deep cavity wounds. This biocompatible platform hydrogel may also act as a delivery vehicle for cytokinesis, proteins, growth factors, biomarkers, and will serve as an ideal matrix for stem cell delivery and tissue engineering, including applications in cosmetic, medical device, biological, and environmental markets.

The copolymer and/or hybrid polymer network may be produced from any desired ratio of polysaccharide to polymer derived from epoxide monomers such as poloxamer. The ratio of polysaccharide to polymer derived from epoxide monomers may be from 1:99 to 99:1. In certain embodiments, the ratio of polysaccharide to polymer derived from epoxide monomers may be from 30:70 to 70:30.

The hydrogel comprising a polysaccharide and a poloxamer may be customized by adjusting various properties of the components and process. The degree of cross-linking will affect the properties of the hydrogel such as pore size. For example, in an e-beam cross-linking process, pore size can be adjusted during the irradiation/curing process by adjusting the strength or exposure time of the beam current. As the reaction mixture moves under the e-beam, the three dimensional structures can be controlled to produce a gel with pore sizes related to the absorbed dose. A higher beam current used in a cross-linking process will result in smaller pore sizes while a smaller absorbed dose from the e-beam will result in a larger internal volume of the pore.

The polysaccharide and poly(epoxide) may be cross-linked with any polymerization process or appropriate cross-linking reaction including radical polymerizations, emulsion polymerizations, controlled polymerization, UV initiated cross-linking, e-beam curing, or other polymerization process. In one embodiment, described herein, is a unique electron beam curing process during which an aqueous solution of two monomers containing "hard" and "soft" groups on a somewhat flexible backbone undergo a spontaneous reorientation or self-arrangement, for example, "soft" groups tend to approach other "soft" groups and the "hard" groups tend to approach the "hard" groups. The breadth of the distribution of so called hard and soft groups can be modified by incorporating other monomers in the same families.

As the narrow beam of ionizing radiation passes through the solution of oriented monomers, the hydrogel is formed containing pores which will attract "hard" and "soft" ions or molecules, which are used as pharmaceuticals. The process will have a significant effect on the rates of diffusion of the pharmaceuticals out of the hydrogel membrane. It may be desirable to increase the elution rate of a given drug from the membrane. Choice of membrane and standard elution rates will provide a hydrogel with a unique handle in product desirability.

Further, the ratio of polysaccharide to poly(epoxide), the molecular weight of the polysaccharide and/or the poly(epoxide), the chemical composition of the polysaccharide and/or the poly(epoxide), the relative lengths of the ABA block of the poloxamer, the degree of self-organization prior to cross-linking, the cross-linking functionality, as well as other factors may affect the physical and chemical properties of the hydrogel. For example, the mechanical strength of the hydrogel or polymeric network can be adjusted by more or less polysaccharide (in some embodiments, dextran) which will produce a different hydrogel or polymeric network with different mechanical strength and a different time controlled delivery of a drug for drug delivery applications.

In one embodiment of the hydrogel derived from dextran and poloxamer, the hydrogel is a biodegradable, large capacity hydrogel that guarantees a safe, sustained, and controlled delivery system for drugs and biomedical applications. The non-toxic, biocompatible, thermal-responsive, and biodegradable delivery system has been synthesized as a hydrogel from the polymerization of modified monomers of dextran and poloxamer. Dextran, a bacterial polysaccharide, has long been employed as an IV blood substitute and is considered non-toxic. Dextranase, found throughout the body, can enzymatically degrade dextran.

Poloxamers are biodegradable and offer a temperature responsive feature. The elevated temperature and narrow range of the human body offers an ideal trigger for thermal-responsive hydrogel release. This new hydrogel molecule will be studied to determine the best formulation for wound healing applications.

Based upon the results of a deswelling study, five hydrogels were produced from the Dextran:poloxamer ratios of 10/90, 30/70, 50/50, 70/30, and 90/10. These studied hydrogels varied in composition and characterization as indicated with regard to the concentrations of monomers and the degree of crosslinking. The gels were evaluated regarding their physical release (drug delivery capability) and structural properties and the extent of hydration.

In further studies, cations (for example, iron, zinc, and/or silver) known to promote wound healing will be incorporated and studied for drug release data. The luciferin/luciferase biomarker will be incorporated into embodiments to serve as visual evidence of the degree of gel delivery. The temperature effect of various embodiments of the hydrogel will be determined by use of porcine cadaver skin maintained at 98.6 degrees to simulate human body temperature. Ambient controls models may be used to gauge performance of the temperature release feature of hydrogel.

The hydrogels may comprise further additives. Some agents of therapeutic benefit proposed for addition to the hydrogel may include, but are not limited to, any type of antibiotic, gallium salts (gallium salts have been shown to kill

*Pseudomonas Aeruginosa* and disrupt biofilm formation in wounds and particularly burn wounds), silver ions which are known to be bacteriostatic, metal chelators such as EDTA, transferrin, lactoferrin, siderophores, and/or other proteins such as proteins that bind iron may be bacteriocidal because bacteria require free iron for growth, chlorohexidine or any other type of antiseptic compound might be a good choice, cell wall hydrolytic enzymes, such as the phage-derived lysins or lysostaphin, or other enzymes capable of being bacteriolytic for select Gram-positive organisms, proteins such as dispersinB or glucuronidase which are capable of disrupting biofilm formation, bacteriocins or other proteins that perforate the outer membrane of Gram-negative organisms, bacteriocidal peptides, such as defensins, histatins, protegrins, tachyplesins, and thionins, quorum sensing inhibitors that disrupt bacterial signals when to change growth patterns or respond to external stress, fibrinogen, thrombin, and Factor 13 for formation of blood clots which are particularly useful for field dressings of battlefield wounds, growth factors, cytokines, or chemokines (C5a or interleuikin-8) that are chemo-attractant for neutrophils and other immune cells, bioengineered LSE' and Human Skin Allograt/nDS "overlay" wound moisture dressing, and stem cells, for example.

The network may be cross-linked by any cross-linking means such as addition of compounds that produce free radicals to cross-link the unsaturated polymers, radiation with high energy electrons, or exposure to ultraviolet light, for example. Typical free radical initiators include benzoyl peroxide, t-butyl peroxide, and hydrogen peroxide, for example. For ultra violet (uv) light initiation, the energy of the light is proportional to the voltage of the source, typically 50, 100, 500, or 900 volts. Gamma Rays initiation may be performed with cobalt-60 as a radioactive source. Machine generated high energy electrons, for example, Van deGraff generator or GE and Nissen High voltage where the energy is related to the eV and amperage of the source.

Alternate Formation and Methods of Saccharide/Poly(Epoxide) Hydrogel

A substitution of meth-acrlylate in the formation of the dextran-acrylate and the pluronic-diacrylate can also deliver the synthesis of the polysaccharide/poly(epoxide) hydrogel. Indeed, this may be a more desirable clinical synthetic protocol more readily approved by FDA under GMP production facilities. Any stereoisomer of the poloxamer, such as r-PLURONIC™, may be used.

The polysaccharide/poly(epoxide) hydrogel, can also be polymerized through other chemical cross-linking methods, for example, peroxide, benzoyl peroxide, t-butyl peroxide, and Hydrogen Peroxide. All of these can produce free radicals and crosslink certain unsaturated polymers.

In addition to chemical cross-linking via ultra-violet light, the polysaccharide and poly(epoxide) may also be polymerized through physical cross-linking, for example, ultra high heat lamps, physical cross-linking, crystallization, hydrogen bonding, etc. Further, high energy electrons can disrupt certain bonds in the polymer molecule initiating crosslinking. Among these are gamma rays (highest energy of all) and radioactive cobalt-60 radioactive source where the energy is related to concentration of $Co^{60}$ in the source.

E-beam cross-linking may be used to produce the polysaccharide/poly(epoxide) hydrogel. Indeed, machine generated high energy electrons (e-beams) may be the preferred production route for the production of a hydrogel in an FDA approved market. This technique offers standardization and reproducibility with large production yield and the environmental advantage that the process does not create chemical waste.

Wound Healing

Embodiments of a drug delivery system or a wound healing system comprise a thermo-responsive biodegradable polymeric hydrogel, which in certain embodiments comprises dextran and poloxamer. From a structural point of view, dextran has reactive hydroxyl groups that can be modified to form reactive end groups, which produce cross-linking via photochemical treatment. The dextran precursor is both enzymatically and hydrolytically degradable. The poloxamer is both water soluble and temperature sensitive. The capability of dispensing a wound healing solution can be facilitated by body temperature over a period of time and will result in a controlled and continuous wound therapy for patients.

Embodiments of the hydrogel for wound healing applications comprise a network of polysaccharide cross-linked with poly(epoxides) and therapeutic agents incorporated into the network. In embodiments for wound healing, the therapeutic agents may promote the recovery of wound tissue, antibacterial, pH buffering and/or bacteriostatic. Such hydrogels may be a unique blend of cationic, anionic, and hydrophobic functional monomers optimized for favorable release properties of the molecules from the hydrogel and hydration of the wound surface. The release of the healing agents may be controlled by response to changes in pH and/or temperature causing the hydrogel to swell.

Specific embodiments of the wound healing agents may comprise a solution comprising zinc ions, silver ions and iron ions. The hydrogel will allow for controlled release of the healing agents of the solution into the wound as well as maintaining the moisture required for proper wound healing.

Various concentrations of zinc and iron may be incorporated in solution to adjust or control release properties of the hydrogels. These components will be incorporated into a hydrogel during synthesis via an aqueous solution.

A wound healing solution may comprise, for example, 5 to 30 mg/L of zinc, 5 to 50 mg/L of iron (in the form zinc chloride and iron sulfate, for example), approximately 100 mg/L sulphuric acid, and water. An acetate buffer with a low pH may also be incorporated into the hydrogel. The acidity of the solution keeps the pH below 3.0, which has also been shown to improve the recovery time of wounds. The low pH also may allow the hydrogels to change formation, releasing the healing agents.

Silver may also be incorporated in embodiments of the wound healing hydrogels described herein. The silver, which has been shown to have antibacterial properties, may be added in conjunction with zinc and/or iron or separately. The concentration of silver may be in concentrations from 5 to 50 mg/L for the wound healing solution.

One embodiment of the hydrogels for wound healing described herein comprise a Zinc:Iron solution comprising zinc cations at 0.030 mgs/ml and iron cations at 0.0195 mgs/ml in sulfuric acid solution of pH 3.0.

Some embodiments of the hydrogel comprising a network having polysaccharides cross-linked with poly(epoxides) are pH tolerant. The hydrogel may be loaded with high or low pH solutions without significant effect on its properties. For example, acidic wound healing solutions may be loaded into the hydrogel.

An embodiment of the drug delivery system comprises a polysaccharide cross-linked with poloxamer to form a hydrogel, and a wound healing composition within the hydrogel. Embodiments of the wound healing composition may comprise highly acidic (pH 3 to pH 2, for example) wound healing solutions. Embodiments of the highly acidic wound healing solutions may comprise cations (for example, cations of Zn, Ag, and Fe) and/or bacterialstatic agents in trace or greater amounts. A biocompatible gel that releases controlled continuous cations in optimun pH with moisture to the wound can be provided with the saccharide/poly(epoxide) hydrogels.

Patients with wound(s) that will not heal with standard treatment may be treated with blood factors that are extracted from their own blood and encapsulated in the saccharide/poly (epoxide) hydrogel for wound healing. A hydrogel patch may be applied to the patient's wound via a wound healing dressing (Hydrogel+Blood Factors+Dressing and additional components to stabilize the blood factors or provide additional wound healing) to apply directly to said patient wound(s) for prolonged controlled therapy and accelerated wound closure.

Blood factors may be extracted and applied to help heal a wound. In one embodiment, Dextran-Poloxamer hydrogel may provide delivery of blood factors with controlled release and prolonged therapy via a non-adhering hydrogel wound healing dressing dispensing encapsulated patient-harvested (or provided) blood factors.

An embodiment of the wound healing patch may include a liquid impermeable outer layer, a layer of hydrogel, a scrim and an additional layer of hydrogel.

Translational Medicine Applications

Nanogels are nanosized networked of chemically or physically cross-linked polymers that swell in an appropriate solvent. The nanogels may be nanoparticles of polymeric hydrogels. Nanogels include nanoscale materials for drugs, pharmaceutical, nanomedicines, proteins, genes, and imaging agents, for example. Nanogels have high loading capacities that are unique among pharmaceutical nanocarriers. Loading of the agents is often achieved through self-assembly mechanisms including Van der Waals and/or hydrophobic interactions between the agent and the polymer matrix. Embodiments of the hydrogel comprising polysaccharides cross-linked with poly(epoxides) (such as a poloxamer) may form a protective degradable layer around the therapeutic agent.

Nanogels may be produced by chemical synthesis by polymerization or copolymerization, chemical cross-linking of the polymeric chains of polysaccharide and poly(epoxide) and/or physical self-assembly of the polymers. Polymerization or cross-linking may be carried out in colloidal dispersions to control the size of the nanoscale hydrogels. In this case, cross-linking agents may be added to the collodial dispersions. Embodiments of the nanogel may have both hydrophobic regions and hydrophilic regions.

The polymerization process may be a reverse microemulsion copolymerization process or cross-linking process. Chemical cross-linking in a microemulsion may be used to prepare nanogels of polysaccharide cross-linked with poly (epoxide). A multifunctional polysaccharides may be cross-linked with a functionalized poloxamers in an microemulsion. The nanogel may be a hydrogel comprising a poloxamer core surrounded by a polysaccharide shell. The swelling of a nanogel may be controlled by several factors including, but not limited to, cross-linking agent concentration, pH, temperature, composition and chain length of the polymeric precursors, for example.

Embodiments of the nanogels may comprise a nominal diameter between 1 nm and 1000 nm. In other embodiments, the nanogels may comprise a nominal diameter between 10 nm and 500 nm. For certain medicinal applications, embodiments of the nanogel may comprise a nominal diameter between 20 nm and 300 nm.

EXAMPLES

A biocompatibnanoDERM Sciences, Inc. al responsive hydrogels that employ the block copolymer poloxamer.

An embodiment of the hydrogel is a dextran-based hydrogel molecule derived from dextran-acrylate esters and poloxamer-diacrylate esters crosslinked to create this new polymer. See Formula 2.

Formula 2: Embodiment of dextran-poloxamer Hydrogel

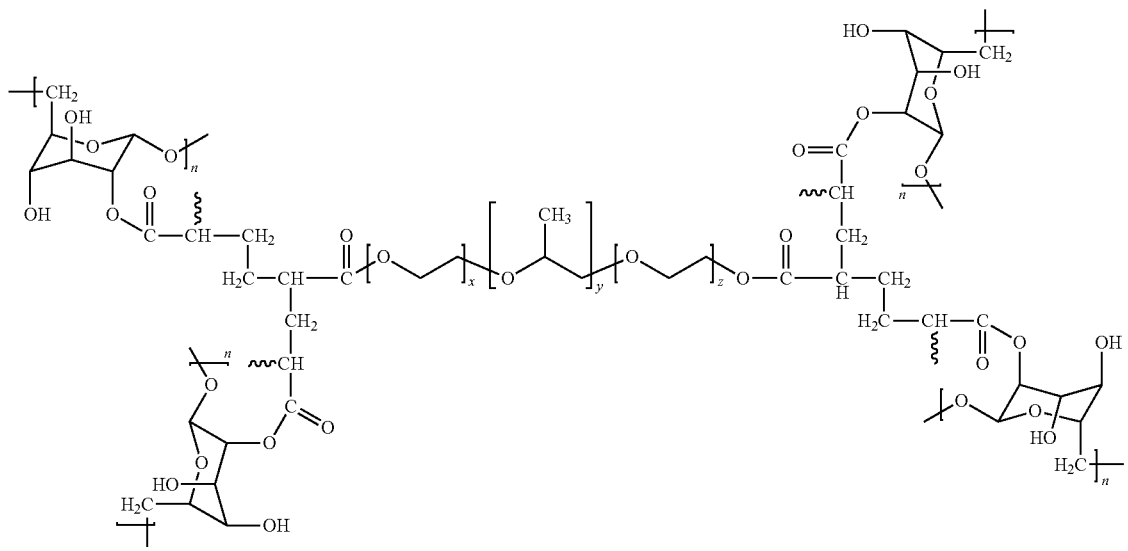

From a structural aspect, dextran has reactive hydroxyl groups (for example, —OH group) that can be modified to form hydrogels via crosslinking such as, but not limited to, photochemical or e-beam crosslinking, for example.

Materials and Procedures: Dextran (DEX) of MW 43,000, acryloyl chloride, pluronic F-127 (F-68), triethylamine, polyethylene glycol (PEG) of MW 8,000 will be purchased from Sigma Chemical Company (St. Louis, Mo.). Dextran will be dried in an oven for 1 hour at 60° C. before use. 2-Hydroxy-1-[4-(hydroxyethoxy)phenyl]-2-methyl-1-propanone (Irgacure 2959) will be purchased from Ciba Specialty Chemicals Corporation.

Example 1

Synthesis of Dextran-Acrylate

Figure 2:
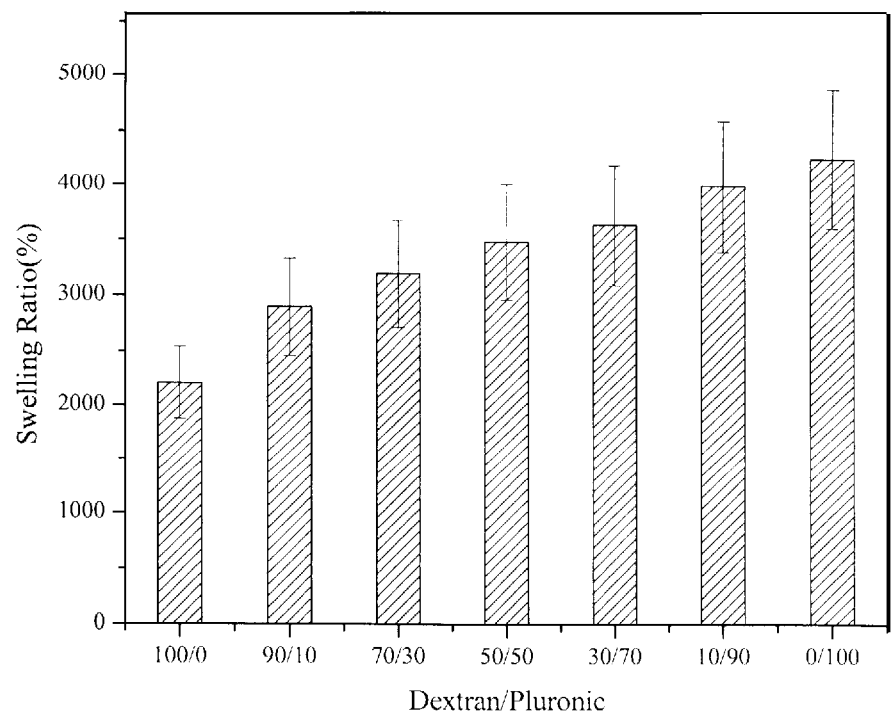
FIG. 2 is a graph of the results of the swelling test for the cross-linked dextran/poloxamer hydrogel.

Dextran was functionalized to produce an enzymatically and hydrolytically bridgeable dextran precursor. The synthesis of dextran-acrylate is shown in FIG. 2. To incorporate cross-linkable double bonds and hydrolytic ester group, acrylate group is incorporated into dextran. At room temperature, pre-dried dextran (2.0 g) was dissolved in anhydrous DMSO (24 mL) under dry nitrogen gas. Triethylamine (0.4 mL) was injected into the solution at room temperature dropwise, and then acryloyl chloride (0.2 mL) was added dropwise. The reaction mixture was stirred at room temperature for three hours. The resulting polymer was precipitated in cold excess isopropanol. The product was further purified by dissolution and precipitation in DMSO and isopropanol, respectively. The resulting dextran-acrylate was dried at room temperature under vacuum for 48 hours and stored in a cold dark place before further use. Thus, the enzymatically and hydrolytically degradable dextran-acrylate is obtained. See Equation 1.

Equation 1: The synthesis of dextran-acrylate

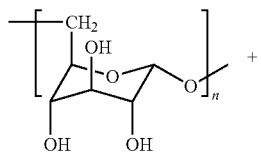

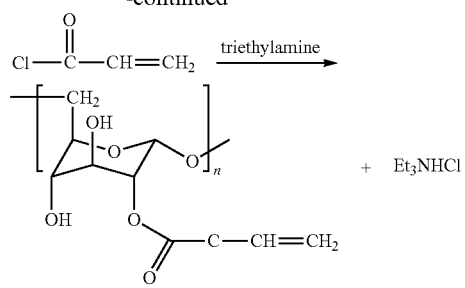

Example 2

Synthesis of Pluronic-Diacrylate

The equation for synthesis of pluronic-diacrylate is shown in Equation 2. Pluronic F-127 (8.0 g) was pre-dried and then dissolved in anhydrous benzene under nitrogen atmosphere. Triethylamine (1.4 mL) and acryloyl chloride (0.8 mL) were subsequently added. The reaction mixture was stirred for 3 hours. The resulting solution was filtered and the polymer is obtained by precipitation in cold hexane. The resultant pluronic-diacrylate was further purified three times by dissolution and precipitation with benzene and hexane, respectively. The pluronic-diacrylate was further dried in a vacuum oven for 24 hours before further use.

Equation 2. The synthesis of pluronic-diacrylate

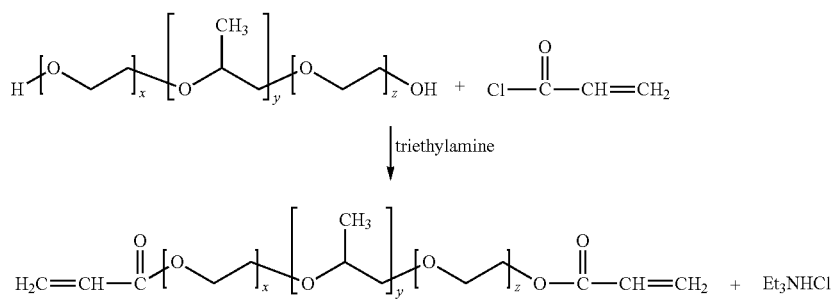

Example 3

Preparation of Hydrogel

The biodegradable dextran-based hydrogels was produced through UV photocrosslinking. The initiator, Irgacure 2959 (2-hydroxy-1-[4-(hydroxyethoxy)phenyl]-2-methyl-1-propanone) was first dissolved in hot water in a vial. The dextran-acrylate and pluronic-diacrylate precursors were added to the above initiator solution and stirred well at room temperature at predetermined feed ratios. The solution obtained was irradiated with UV light for 10 minutes. The resulting hydrogels were washed in distilled water for 48 hours to remove unreacted precursors. The swollen hydrogel will be either freeze dried or oven dried. See Equation 3: Synthesis of Dextran-Pluronic Hydrogel.

Equation 3: Synthesis of Dextran-Pluronic Hydrogel

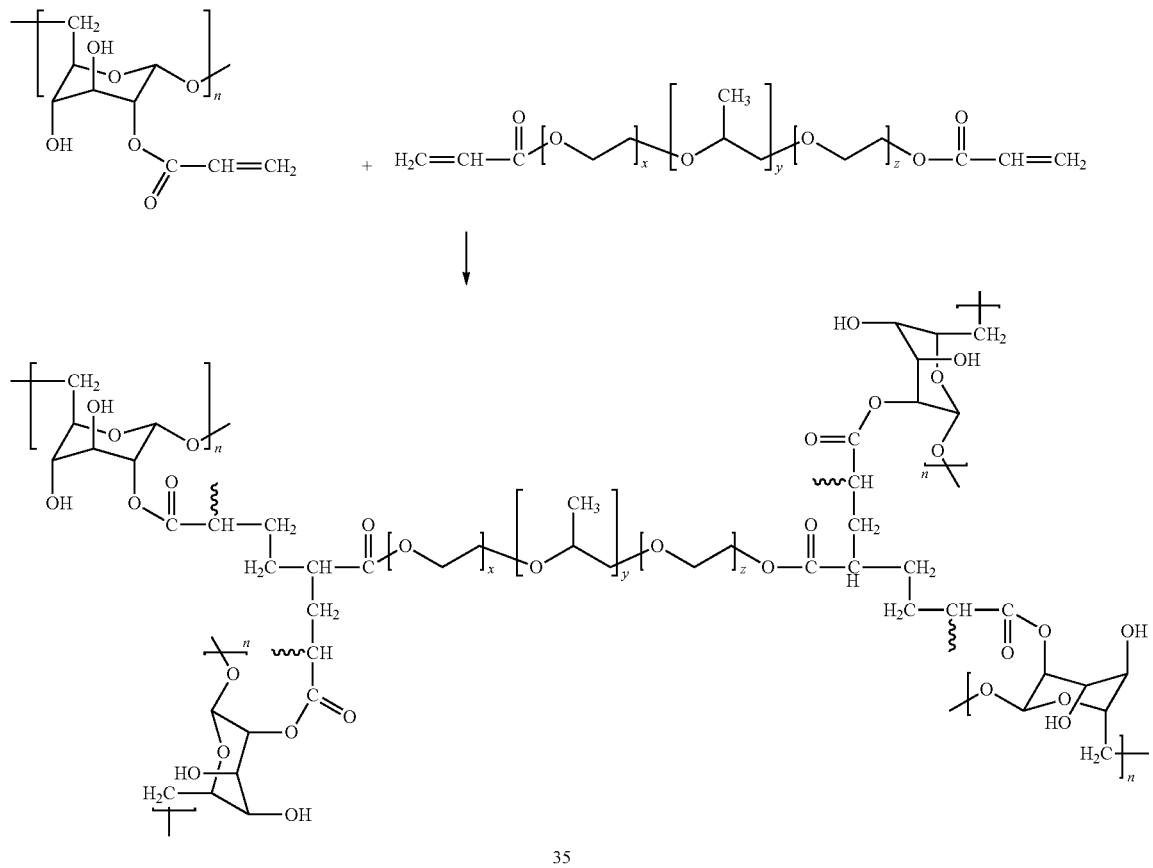

Example 4

Swelling Study of Dextran Hydrogels

The swelling ratio of dextran-based hydrogels was gravimetrically determined. Predried hydrogel specimens were immersed in distilled water at body temperature. The swollen hydrogel samples will be removed from water at predetermined intervals and weighed after wiping off excess water from the surface with a wet filter paper. The swelling ratio is then calculated according to the following formula:

Swelling ratio=$((W_{s,t}-W_d)/W_d) \times 100\%$, wherein $W_d$ is the weight of dry hydrogels, and $W_{s,t}$ is the weight of swollen hydrogel samples at time t. The hydrogel is assumed to reach a state of swelling equilibrium or water equilibrium when there was no difference in swelling ratio between two adjacent intervals.

Deswelling Study of Dextran Hydrogels

The deswelling kinetics of gels was measured gravimetrically at 37° C. after wiping off water on the surface with moistened paper towels. Before the measurement, the gel samples will reach equilibrium swelling state in distilled water at 38° C. The weight changes of gels were recorded at the course of deswelling at regular time intervals. Water retention ($W_r$) is defined as $W_r=(W_{s,t}-W_d)/W_w \times 100\%$, where Ws is the weight of the water in the swollen gel, and the other symbols are the same as above.

Statistics

All measurements of hydrogel properties will be performed on either duplicate or triplicate samples with triplicate readings for each data point. One way or two-way ANOVA tests will be performed where appropriate. Significance levels will be set at: *$p<0.05$, $p<0.01$, and *$p<0.001$.

Results

The objective of this step is to prepare biodegradable thermo-responsive hydrogels through the UV-photo-crosslinking and determine their swelling and deswelling properties. The initiator, Irgacure 2959 (2-hydroxy-1-[4-(hydroxyethoxy)phenyl]-2-methyl-1-propanone) was first dissolved in hot water. The dextran and pluronic precursors at predetermined feed ratios were dissolved in above initiator solution. The solution was UV irradiated for 20 minutes for gelation. The resulting hydrogels were washed in distilled water for 24 hours to remove unreacted precursors. The final gel was dried in a vacuum oven at 60° C. for 2 days before further use. The feed composition and the sample ID are listed in Table 1.

It was found that the hydrogels can be in all the range of feed ratios from 100/0 to 0/100 of dextran/pluronic. Under the test condition, the conversion ratio range 50% to 64%. Other conditions will be tested to determine the best gel forming.

TABLE 1

Feed ratio and formation of Dextran/Fluronic hydrogels

| | Sample ID[a] | | | | | | |
|---|---|---|---|---|---|---|---|
| | DP1 | DP2 | DP3 | DP4 | DP5 | DP6 | DP7 |
| Dextran(mg) | 0 | 10 | 30 | 50 | 70 | 90 | 100 |
| Pluronic(mg) | 10 | 90 | 70 | 50 | 30 | 10 | 0 |

TABLE 1-continued

Feed ratio and formation of Dextran/Fluronic hydrogels

| | Sample ID[a] | | | | | | |
|---|---|---|---|---|---|---|---|
| | DP1 | DP2 | DP3 | DP4 | DP5 | DP6 | DP7 |
| Irgacure 2959[b](%) | 0.01 | 0.01 | 0.01 | 0.01 | 0.01 | 0.01 | 0.01 |
| Conversion(%) | 59.26 | 52.97 | 63.94 | 49.42 | 51.69 | 49.46 | 59.43 |

[a]All reactions were carried out for 20 minutes at room temperature.
[b]Initiator: 2-Hydroxy-1-[4-(hydroxyethoxy)phenyl]-2-methyl-1-propanone.

The preliminary swelling data shows the equilibrium swelling of the hydrogel could be reached within 24 hours. The swelling ratio increased from 2200% to 4250% when the Pluronic component increased from 0% to 100%. See FIG. 2.

Prophetic Examples

Example 5

Non-toxic non acrylamide transdermal patches may formed with E-Beam Technology using the biocompatible Dextran-Pluronic formula that will not exhibit an unwanted dermal immune response.

Example 6

Optimum moisture, therapeutic agents, and wound healing solutions may be dispensed by a Dextran Hydrogel Dressing over the duration of the healing process.

Example 7

The natural Dextan Hydrogel affords a hydrated tissue comparable environment for encapsulating cells and offers a biodegradable feature ideal for tissue engineering and stem cell applications.

Example 8

Blood factors may be encapsulated in an optimized natural Dextran hydrogel to increase the blood factor half-life and prolong therapy.

Example 9

A dental implant of antibiotic is inserted into the cavity of a patient preventing infection from a dental implant.

Example 10

A analgesic loaded Dextran gel is implanted during a surgical operation to alleviate prolonged post-operative patient pain.

Example 11

Prepared stem cells are loaded into the natural dextran hydrogel that is tailored for optimum degradation enabling cell growth and maturation.

Example 12

Nanosized Dextran hydrogels that carry cancer biomarkers and cancer therapy are administrated with IV Dextrose to detect and kill cancer cells in the new science of Theranostics.

Example 13

Nanosized (40-60 nanometers) Dextran hydrogels loaded with fluorescent dyes deliver diagnostic fluors for neural imaging.

Example 14

Nonadherent Dressings: Nonadherent dressings are designed not to stick to the wound. Gauze is often impregnated with paraffin or petroleum jelly to provide a nonadherent dressing. However, the impregnate can wear off, necessitating a dressing change and traumatizing new tissue growth. In addition to the impregnated gauze type, nonadherent dressings may consist of an absorbent pad faced by a preformed nonadherent film layer.

Hydrogels are complex lattices in which the dispersion medium is trapped rather like water in a molecular sponge. Available hydrogels are typically insoluble polymers with hydrophilic sites, which interact with aqueous solutions, absorbing and retaining significant volumes of fluid.

Dextran Hydrogel's high water content is optimized as a platform Phosphate Buffered Saline (PBS) non-adherent dressing that dispenses wound healing moisture increasing epidermal healing. In liquefying, hydrogels conform to the shape of the wound and their removal is untraumatic.

Example 15

Bioabsorable Dextran-Pluronic Hydrogel may be loaded with hemostats staunching blood flood and then degraded in vivo. As such, the hydrogel will not require removal.

Example 15

The biocompatible nano hydrogels described herein comprising a nominal size of 40-60 nanometers are to be loaded with diabetic insulin to produce an oral insulin delivery method. Optimized polymerization of temperature sensitive nanogels achieves a suitable oral delivery of insulin by modified composition of copolymers. Controlled and sustained diabetic therapy is achieved by oral delivery of nanogel-Insulin.

Example 16

A monthly IV injection of insulin loaded, biocompatible, temperature responsive, and biodegradable nano Hydrogels achieves a sustained and controlled release of insulin for diabetic therapy.

Example 17

In Vivo Theranostics via injectable nano hydrogel delivery of cancer biomarkers and cancer therapy.

The invention claimed is:
1. A nanogel comprising:
a polymeric network comprising a plurality of first block copolymeric segments derived from poloxamer monomers, wherein the poloxamer comprises polyoxyethelene segment in the range of 60 wt. % to 80 wt. % and a polyoxypropylene segment having a molecular mass in the range of 2,500 to 5,000 g/mol.;
a plurality of second polymeric segments derived from unmodified dextran; and biocompatible linking groups comprising an ester group, wherein the biocompatible linking groups crosslink the first block copolymeric segments to the second copolymeric segments;
water; and
therapeutic agent, wherein the size of the nanogel is between 1 and 1000 nm.

2. The nanogel of claim 1, wherein the linking groups comprise at least two ester groups.

3. The nanogel of claim 1, wherein the linking groups are derived from an acrylate.

4. The nanogel of claim 1, wherein the hydrogel is capable of retaining a solution having a pH between 2 and 3.

5. The nanogel of claim 1, wherein the dextran has a molecular weight of 43,000 g/mol.

6. The nanogel of claim 1, wherein the therapeutic agent comprises at least one of silver or silver ions.

7. The nanogel of claim 6, wherein the therapeutic agent comprises at least one of zinc, iron and a combination of zinc and iron.

8. The nanogel of claim 7, wherein the therapeutic agent comprises 5 to 30 mg/L of zinc, 5 to 50 mg/L of iron, approximately 100 mg/L sulphuric acid, and water.

9. The nanogel of claim 1, wherein the therapeutic agent is at least one of an antibiotic, gallium salt, silver ions, metal chelators, EDTA, transferrin, lactoferrin, siderophores, proteins that bind iron, chlorohexidine, antiseptic compounds, cell wall hydrolytic enzymes, phage-derived lysins or lysostaphin, enzymes capable of being bacteriolytic for select Gram-positive organisms, dispersin B, glucuronidase, bacteriocins, proteins that perforate the outer membrane of Gram-negative organisms, bacteriocidal peptides, defensins, histatins, protegrins, tachyplesins, thionins, quorum sensing inhibitors, fibrinogen, thrombin, and Factor 13 for formation of blood clots, growth factors, cytokines, or chemokines, bioengineered LSE' and stem cells.

* * * * *